United States Patent
Lin et al.

(10) Patent No.: US 11,935,349 B2
(45) Date of Patent: Mar. 19, 2024

(54) MANAGING ACCESS TO PHYSICAL AREAS BASED ON CAPTURED DIGITAL DATA AND A DATABASE

(71) Applicants: Candice Lin, Campbell, CA (US); Te-Yu Chu, Campbell, CA (US); Phuc Nguyen, Campbell, CA (US); Yuwen Wu, Cupertino, CA (US); Kaoru Watanabe, Sunnyvale, CA (US); Shun Tanaka, Campbell, CA (US); Jayasimha Nuggehalli, Cupertino, CA (US)

(72) Inventors: Candice Lin, Campbell, CA (US); Te-Yu Chu, Campbell, CA (US); Phuc Nguyen, Campbell, CA (US); Yuwen Wu, Cupertino, CA (US); Kaoru Watanabe, Sunnyvale, CA (US); Shun Tanaka, Campbell, CA (US); Jayasimha Nuggehalli, Cupertino, CA (US)

(73) Assignee: Ricoh Company, Ltd., Tokyo (JP)

( * ) Notice: Subject to any disclaimer, the term of this patent is extended or adjusted under 35 U.S.C. 154(b) by 149 days.

(21) Appl. No.: 17/515,023

(22) Filed: Oct. 29, 2021

(65) Prior Publication Data

US 2023/0135861 A1 May 4, 2023

(51) Int. Cl.
*G07C 9/28* (2020.01)
*G06F 8/71* (2018.01)
*G07C 9/29* (2020.01)
*G16H 10/65* (2018.01)

(52) U.S. Cl.
CPC ............... *G07C 9/28* (2020.01); *G06F 8/71* (2013.01); *G07C 9/29* (2020.01); *G16H 10/65* (2018.01)

(58) Field of Classification Search
CPC ........ G07C 9/28; G07C 9/29; G07C 9/00571; G07C 2009/00412; G07C 9/27; G07C 2209/41; G06F 8/71; G16H 10/65
See application file for complete search history.

(56) References Cited

U.S. PATENT DOCUMENTS

| | | | |
|---|---|---|---|
| 8,462,994 B2* | 6/2013 | Ortiz | G07C 9/28 340/5.8 |
| 8,844,811 B1* | 9/2014 | Rogers | G07C 9/00904 235/382 |
| 8,919,645 B1* | 12/2014 | Jones | G07C 9/28 235/382 |
| 9,479,339 B2* | 10/2016 | Bender | H04L 9/3265 |
| 9,483,631 B2* | 11/2016 | Lowe | H04W 12/068 |
| 9,508,207 B2* | 11/2016 | Kalb | G07C 9/00571 |
| 9,548,982 B1* | 1/2017 | Karunakaran | H04L 63/0815 |

(Continued)

*Primary Examiner* — Brian E Miller
(74) *Attorney, Agent, or Firm* — Hickman Becker Bingham Ledesma LLP

(57) ABSTRACT

Techniques for managing access to a physical area are provided. In one technique, first data is extracted from a digital file. Based on identification data within the first data, a database is searched. A data item in the database is identified that matches the identification data. The first data is associated with the data item. After associating the first data with the data item, code data is generated. Encoded data that encodes the code data is then generated. The encoded data is sent over a computer network to a mobile device, or an account, of a user that is associated with the data item.

20 Claims, 5 Drawing Sheets

(56) References Cited

U.S. PATENT DOCUMENTS

| | | | |
|---|---|---|---|
| 9,554,279 B1 * | 1/2017 | Kremer | H04W 4/029 |
| 9,640,002 B1 * | 5/2017 | Grosberg | G07C 9/00174 |
| 9,875,590 B2 * | 1/2018 | Schmidt-Lackner | ......... |
| | | | G07C 9/00571 |
| 9,972,144 B2 * | 5/2018 | Klein | G07C 9/00309 |
| 10,665,047 B1 * | 5/2020 | Terp | G07F 17/0014 |
| 10,923,216 B1 * | 2/2021 | White | H04L 9/3231 |
| 11,011,003 B1 * | 5/2021 | Jafri | G16H 50/80 |
| 11,263,850 B2 * | 3/2022 | Jafri | H04W 12/64 |
| 11,398,122 B2 * | 7/2022 | Terp | G06K 19/06037 |
| 2009/0153291 A1 * | 6/2009 | Larson | G07C 9/00817 |
| | | | 340/5.33 |
| 2015/0007619 A1 * | 1/2015 | Finney | G07F 17/12 |
| | | | 70/264 |
| 2021/0327181 A1 * | 10/2021 | Klein | G16H 10/40 |
| 2021/0327189 A1 * | 10/2021 | Jarvis | G07C 9/20 |
| 2021/0327548 A1 * | 10/2021 | Sparks | A61B 5/1172 |
| 2021/0350649 A1 * | 11/2021 | Jafri | H04W 12/64 |
| 2021/0391041 A1 * | 12/2021 | White | G07C 9/27 |
| 2022/0167154 A1 * | 5/2022 | Ejiri | G06F 21/34 |
| 2022/0301667 A1 * | 9/2022 | Church | G16H 40/20 |
| 2023/0135861 A1 * | 5/2023 | Lin | G07C 9/28 |
| | | | 340/5.7 |
| 2023/0162546 A1 * | 5/2023 | O'Toole | G07C 9/00563 |
| | | | 340/5.52 |

* cited by examiner

MANAGING ACCESS TO PHYSICAL AREAS BASED ON CAPTURED DIGITAL DATA AND A DATABASE

TECHNICAL FIELD

The present disclosure relates generally to improving the management of access to one or more physical areas and, more particularly to, capturing physical document data, and managing access to a physical area by using the captured data and a database.

BACKGROUND

Managing access to buildings, rooms, etc., (referred to herein as "physical areas") has been addressed with modern key card access systems. After being issued a key card (e.g., with radio-frequency identification (RFID) technology), a person may present the key card at a card reader adjacent to a physical area in order to gain physical access to that physical area. If the card reader recognizes an identifier transmitted from the key card, then the person is granted access, which may be in the form of automatically unlocking a door.

However, there is a growing need to add further restrictions to accessing physical areas, particularly in the area of preventing the transmission of communicable diseases. Issuing and deactivating key cards based on the health or vaccination status of an individual quickly becomes an administrative burden, especially for large enterprises.

One approach is for all people who wish to gain access to certain physical areas to travel to certain designated areas where one or more checks are performed, such as checking a vaccination card and performing a temperature test. For example, a person with a temperature within a certain range is granted access to a physical area by the person administering the temperature test. However, this approach is a significant administrative burden that increases the costs of running an enterprise. Also, this approach requires people to administer the checks near the entrance of each physical area when there may be many physical areas to which a person might need access. Furthermore, if a person needs access to one or more of the physical areas on a daily basis, then these checks need to be performed manually on a daily basis.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

General Overview

A system and method for managing user access to physical areas are provided. In one technique, a mobile device generates a digital image of a physical document, such as a vaccination card. The mobile device transmits the digital image over a computer network to a remote computer system, which extracts data from the digital image. The extracted data includes information reflected on the physical document, such as a first name, last name, date of a vaccination, a type of vaccine that was used, and a location of the vaccination. The remote computer system uses, as search terms, the last name and, optionally, the first name to identify a record in an employee database. If a record is found that matches the search terms, then an association is generated that associates the extracted data with the record. The remote computer system generates code data (e.g., an employee identifier or a date of expiration), encodes the code data, and causes the encoded data to be sent to the mobile device. The mobile device provides the encoded data to a device that is located near an entrance of a predetermined physical area. The device or the remote computer system decodes the encoded data and determines, based on the decoded data, whether to grant access to the predetermined physical area.

Embodiments improve computer-related technology by securely storing extracted data about a user, matching the extracted data to a record in an existing database, and transmitting encoded data to a mobile device of the user. The user may then present the encoded data to any one of multiple designated areas to obtain access to physical areas. In this way, administration of manual checks of physical documents, such as vaccination cards, is avoided. Embodiments can also apply to any other type of document used to enter physical areas, i.e., documents other than vaccine cards, PCR test results, and other document relating to disease.

System Overview

Figure 1A:
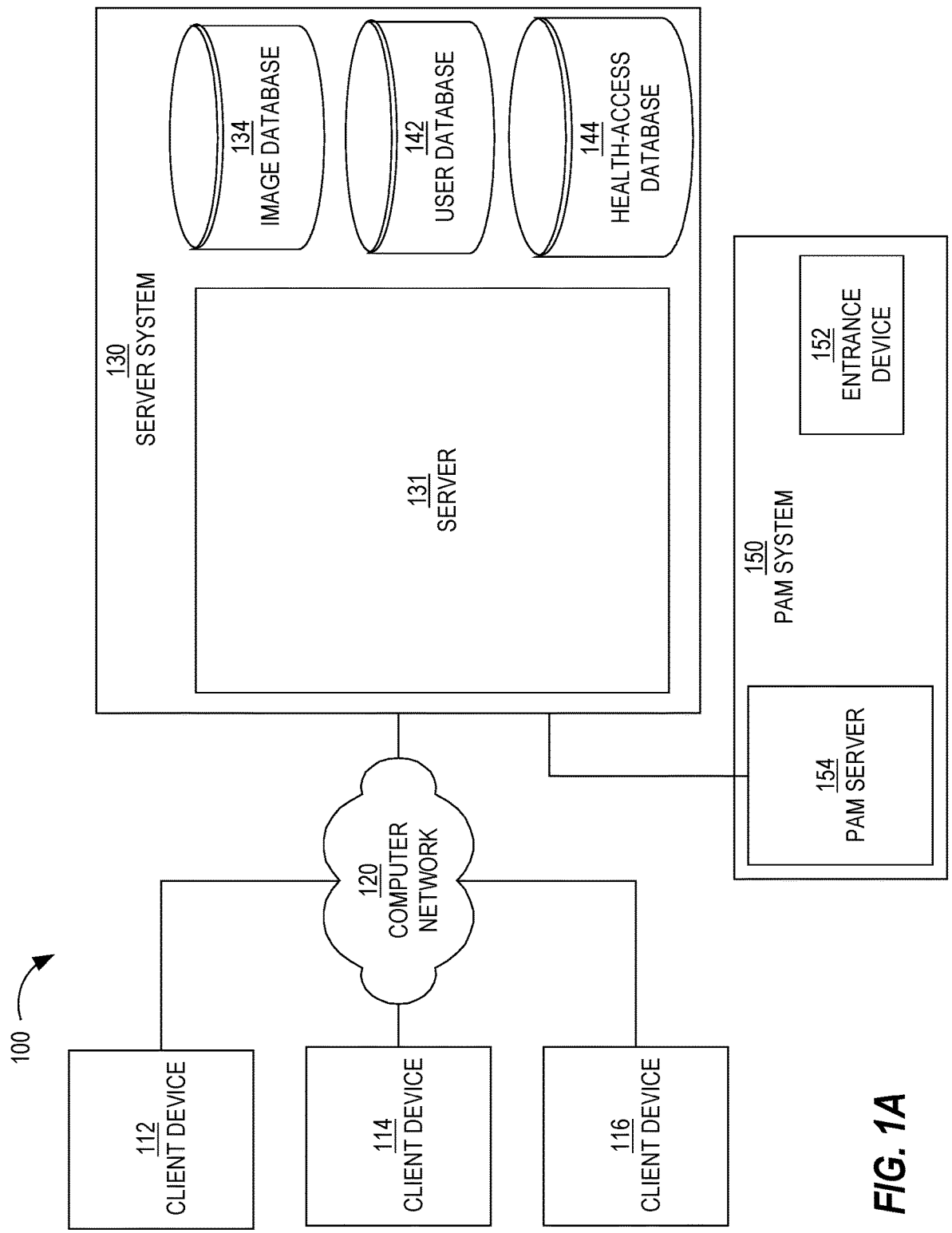
FIGS. 1A-1B are block diagrams that depict an example system for extracting data from image data, securely storing the extracted data, and granting access to a physical area, in an embodiment.

FIG. 1A is a block diagram that depicts an example system 100 for extracting data from image data, securely storing the extracted data, and granting access to a physical area, in an embodiment. System 100 includes client devices 112-116, a computer network 120, a server system 130, and a physical access management system 150.

Client devices 112-116 are communicatively coupled to server system 130 via computer network 120 (e.g., a LAN, WAN, or the Internet). Examples of client devices 112-116 include desktop computers, scanning devices, video game consoles, and mobile devices, such as laptop computers, tablet computers, wearable devices, and smartphones.

One or more of client devices 112-116 may include a digital camera that "takes pictures" or, in other words, generates digital images. The digital images may be in any image format, such as TIFF, GIF, PNG, RAW, PDF, and JPEG. One or more of client devices 112-116 may execute a software application that includes a software application that is configured to communicate with server system 130. For example, the software application may be developed by the entity that owns or operates server system 130. The software application is configured to communicate with the host device's camera. Through the software application, a user of the client device points the camera view toward a physical document, such as vaccination card or a document indicating the results of one or more medical tests, such as a (polymerase chain reaction) PCR test. One or more client devices may scan the vaccine card, a document indicating the results of one or more medical tests, or other document for entering the physical area. Additionally or alternatively, one or more client devices may just send a digital file to server system 130. This may be the case, for example, when a government provides a vaccine card as a digital file.

Server System

As depicted in FIG. 1A, server system 130 includes a server 131, an image database 134, a user database 142, and a health-access database 144.

Figure 1B:
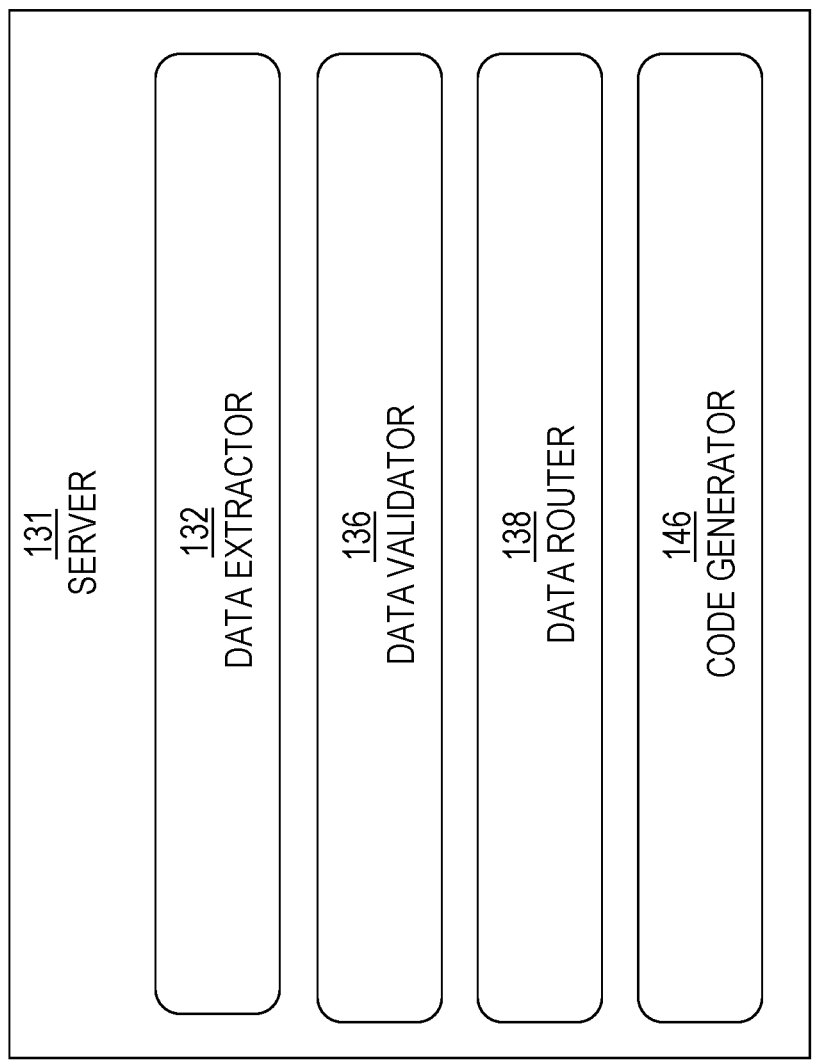

As depicted in FIG. 1B, server 131 comprises a data extractor 132, a data validator 136, a data router 138, and a code generator 146. Server system 130 may include multiple servers. For example, each of data extractor 132, data validator 136, data router 138, and code generator 146 may be implemented in a different server. Each of data extractor 132, data validator 136, data router 138, and code generator 146 may be implemented in software, hardware, or any combination of software and hardware.

Although depicted as functioning separately, two or more of data extractor 132, data validator 136, data router 138, and code generator 146 may be implemented in the same computing component (e.g., software program). The function of data validator 136 is optional.

Although the elements of server system 130 are depicted as being the only element of its kind in server system 130, server system 130 may include multiple of one or more of these elements, such as multiple user databases and multiple data validators. These additional elements may be mirrored versions of the original elements in order to provide backup in case the corresponding elements fail. Additionally or alternatively, if there are multiple user databases, then each user database may contain information about a different set of users, each set of users corresponding to a different organization or enterprise. For example, one user database contains information about employees from company A while another user database contains information about employees from company B.

Additionally, system 100 may include multiple server systems 130.

Data Extractor

Data extractor 132 receives image data from a client device (e.g., client device 112). Data extractor 132 extracts information from the image data. For example, data extractor 132 performs optical character recognition (OCR) on the image data. Data extractor 132 may store image data in a record of image database 134, which is optional. Each record in image database 134 may include a record identifier, image data, the extracted data for that image data, a device identifier (e.g., an IP address or a MAC address) that identifies a device that transmitted the image data to server system 130, and/or a user identifier (e.g., an employee identifier) that identifies a user that operated the device or was logged into the device when the device transmitted the image data.

While data extractor 132 is depicted as executing in server system 130, a portion of data extractor 132 may execute in a client device, such as client device 112. For example, an OCR function may be executed in the client device. Data extractor 132 extracts predetermined data (e.g., first name, last name) from a digital file (e.g., a digital image). Data extractor 132 may extract predetermined data according to a parsing rule.

In embodiment, one or more parsing rules are defined to sample data from a sample image. For example, one parsing rule is used to extract a last name, while another parsing rule is used to extract a first name. After the parsing rules are defined, portions of an instance of image data are automatically extracted using the one or more parsing rules. A description of implementing parsing rules is found in the following related applications: U.S. patent application Ser. Nos. 16/805,663 and 16/587,418.

In an embodiment, data extractor 132 generates a confidence level of each extracted data item from the image data. The confidence level indicates how confident data extractor 132 is in extracting correct text and in associating that text with an appropriate field name, such as Last Name, Vaccination Date, etc. Thus, data extractor 132 may assign a high confidence level to extracting "Davis" but assign a low confidence level in associating "Davis" to any of the available data fields, such as Last Name and First Name.

In an embodiment, in addition to image data, client device 112 transmits an identifier that uniquely identifies the user of client device 112. For example, if client device 112 executes a software application that is registered with the entity that owns or manages the data in user database 142, then the software application includes a user identifier or device identifier that is included in one of the records in user database 142. Thus, data extractor 132 may also store the identifier in the record that includes the corresponding image data.

Data Validator

Data validator 136 (which is optional) validates data that data extractor 132 extracted from image data. For example, data validator 136 validates whether a set of predefined field names have been extracted along with corresponding values: last name, first name, a date, a recognized vaccine type, a vaccination location, a lot number, and/or a clinic site. If a predefined field name has not been extracted, then data validator flags the extracted data (and/or the corresponding image data). "Flagging" involves storing data that indicates that the extracted data is incomplete. Similarly, if a value for a predefined field name has not been extracted, then data validator 136 flags the extracted data (and/or the corresponding image data). A reason why predefined field names and/or corresponding values might not be extracted by data extractor 132 is because the names or values may be unrecognizable due to poor penmanship, folds in the physical document that obscure some letters, and physical wear from sunlight or liquids.

In an embodiment, an administrator device (not depicted) has access to image data and corresponding extracted data in order to manually validate extracted data. A user of the administrator device may limit manual validations to image data that has been flagged. In this way, relatively few manual validations may need to be made.

In a related embodiment where a confidence level is determined for each of one or more extracted data items (i.e., field names and corresponding values), data validator 132 determines, based on a confidence value of an extracted data item, whether to store notification data and/or send a notification message to an account associated with an administrator user or to the administrator device. For example, if a confidence level of a particular extracted data item is less than a predefined confidence threshold, then data validator 132 sends a notification message to the administrator device. A user of the administrator device logs into server system 130 and accesses image database 134 to view the image data in conjunction with any extracted data items.

Data Router

Data router 138 receives extracted data that has been validated. Data router 138 may receive the extracted data directly from data validator 136 or from image database 134. For example, data router 138 periodically checks image database 134 for new or updated records. Each record may include a field value that indicates whether the corresponding extracted data is complete or has the necessary information to confirm that the corresponding user has passed a health check or been vaccinated. As another example, data validator 136 sends a row identifier to data router 138 when data validator 136 determines that the extracted data is complete. Receipt of the row identifier triggers data router 138 searching user database 142. In this way, data router 138 is not required to periodically search image database 134.

Data router 138 searches for a record in user database 142, which stores data about multiple users. For example, user database 142 may be an employee database that stores data about multiple employees of an enterprise or company. The search criteria that data router 138 uses to search user database 142 may include a user identifier, a device identifier, a last name, and a first name. If an identifier is used to search user database 142, then no other search criteria may be required to search user database 142 since the identifier may be uniquely identifying, such as a device identifier or an employee identifier. If an identifier is not available, then data router 138 may use last name and first name as search criteria to search user database 142.

Data router 138 generates association data and stores the association data in an appropriate record in health-access database 144 when data router 138 identifies a corresponding record in user database 142 based on the extracted data. As described in more detail herein, data router 138 may store the user/employee identifier to the record of health-access database 144. In this case, the user/employee identifier (which is found in user database 142 and stored in a record of health-access database 144) is the association data. The generation of the association data and storing the association data are associating the extracted data with the user/employee identifier.

If contents of health-access database 144 are stored in image database 134 (as described in more detail herein), updating one or more fields of a corresponding record in the image database 134 with data from user database 142 is the "associating." In this case, the updated data of the field is the association data. In other words, any data that associates user/employee data with the extracted data can be the association data.

Health-access database 144 includes, for each record, (1) extracted data, i.e., data that has been extracted from image data and (2) data from user database 142. Thus, each record in health-access database 144 includes data items from corresponding image data (e.g., a first name, a last name, a date of a vaccination, a type of vaccine, a location of the vaccination) and one or more data items from user database 142 (e.g., a user/employee identifier, authorized physical areas, times of authorized access). A user identifier (from user database 142) in a record of health-access database 144 allows a lookup into user database 142 given a record in health-access database 144.

A record in health-access database 144 may be updated in response to an update to a corresponding record in user database 142. For example, if an employee leaves the company, then the corresponding record in user database 142 may be deleted (or updated to indicate the departure). Also, the corresponding record in health-access database 144 is similarly deleted or updated.

Although health-access database 144 is depicted as a separate database from user database 142, the data in health-access database 144 may be stored in user database 142. For example, user database 142 may be updated to include one or more fields for extracted data, such as date of a vaccination, type of vaccine, and location of the vaccination. Alternatively, the data in health-access database 144 may be stored in image database 134. For example, image database 134 may be updated to include one or more fields for the extracted data and employee identifier, email address, and/or phone number, which originates from user database 142.

In some situations, a record in user database 142 might not be found based on extracted data. This may result from at least a portion of the extracted data being inaccurate (e.g., last name of "Smith" is extracted as "Smyth") or from an incomplete user database 142. If a matching record is not found, then data router 138 may cause a notification message to be transmitted to the client device that transmitted the corresponding image data. Additionally or alternatively, data router 138 may cause a notification message (e.g., a SMS message, an email message, or an app message) to be transmitted to a computing device of an administrator user of server system 130. Upon user selection of a link in the notification message, server system 130 presents at least a portion of (1) the extracted data and (2) the image data on a screen of the computing device. GUI controls may be included in the presentation to allow the administrator user to modify the extracted data if the administrator user determines that the extracted data does not match corresponding data reflected in the image data. For example, the administrator user may type in a last name that is different than the last name that data extractor 132 detected.

Code Generator

Code generator 146 generates a code for a new record in health-access database 144 or for extracted data that has been validated. The code (or an encoded version thereof) is eventually transmitted to a device of a user, who will present the code (or the encoded version) to a code reader that is adjacent to an entrance of a physical area to which the user seeks access. Thus, the code may be tied or linked to the new record in health-access database 144 (or to the appropriate record in user database 142). Alternatively, the code may be a particular value that affirms that the associated user has passed a health check, such as receiving a vaccination or passing a medical test, such as a PCR test that tests whether the user is infected with a particular virus.

In an embodiment, code generator 146 generates a code using one or more encoding techniques. Example encoding techniques include a bar code generation technique, a two-dimension code generation technique (e.g., a QR code generation technique), and encryption, such as public-private key encryption. In the latter scenario, code generator 146 uses a private key to encrypt the code, resulting in encoded data.

After a code is generated, the code (or an encoded version thereof) is transmitted over computer network 120 to a client device, such as client device 112. Transmission of the code (or encoded data) may be performed by code generator 146 or another element of server system 130.

Transmission of the code (or encoded data) may be performed in one of multiple ways. For example, a text message (that includes the encoded data) is transmitted based on a phone number that is retrieved from the matching data item located in user database 142. As another example, an email message (that includes the encoded data) is generated and sent to an email address that was retrieved from the matching data item. As another example, an application message is sent to an application that is executing on the mobile device. The application or mobile device is identified based on an identifier for the mobile device, where the identifier is retrieved from the data item.

The client device that receives the code/encoded data may be a mobile device that transmitted the image data, which resulted in server system 130 extracting data from the image data, identifying a record in user database 142 based on the extracted data, and generating the code in case a record in user database 142 is found. If the code is a value that indicates that the corresponding user is granted access to a physical area, then the code may be sent to PAM system 150, which is described in more detail herein.

Code Generation Process Overview

Figure 2:
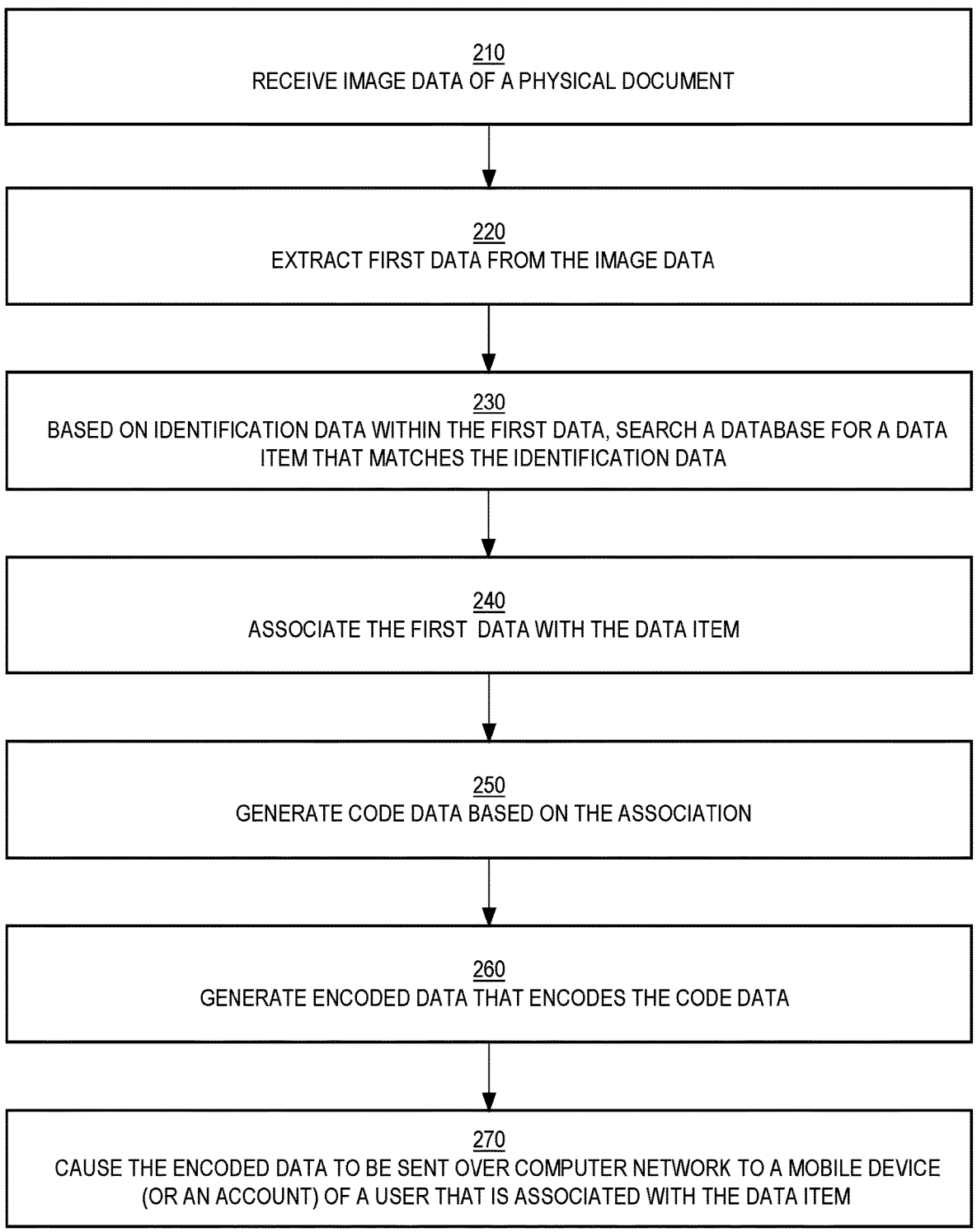
FIG. 2 is a flow diagram that depicts an example process for providing encoded data to a user's computing device, in an embodiment.

FIG. 2 is a flow diagram that depicts an example process 200 for providing encoded data to a user's computing device, in an embodiment. Process 200 may be performed by different elements of server system 130.

At block 210, image data of a physical document is received, such as over computer network 120. Block 210 may involve receiving the image data from a mobile device, such as client device 112, that includes a digital camera that generated the image data. Alternatively, the physical document may have been scanned by a scanning machine that is communicatively coupled to server system 130.

At block 220, first data (referred to as "extracted data") is extracted from the image data. The extracted data includes information reflected on the physical document, such as one or more names of an individual and one or more health-related items. Block 220 may be performed by data extractor 132, which implements one or more OCR techniques.

At block 230, based on identification data within the extracted data, a database is searched for a data item that matches the identification data. Block 230 may be performed by data router 138. The identification data may be a first name and a last name. Alternatively, the identification data may be a user/employee identifier, which may or may not be separate from the extracted data.

At block 240, the extracted data is associated with the data item. Block 240 may involve generating data that associates with extracted data with the data item. The generated data may be a user/employee identifier that is associated with both the extracted data and the data item. The generated data essentially links the extracted data with the data item in the database.

At block 250, code data is generated based on the association data. The code data may include (a) a portion of the extracted data, such as some of the vaccination-related data; (b) a randomly-generated number that is unique to the corresponding user; and/or (c) a value that indicates that the user is authorized access to one or more physical areas.

At block 260, encoded data that encodes the code data is generated. The encoded data may be a QR code, a bar code, or a series of alphanumeric characters that is a result of encrypting the code data using an encryption key.

At block 270, the encoded data is caused to be sent, over a computer network, to a mobile device, or an account, of a user that is associated with the data item. Block 270 may involve sending the encoded data to a particular software application executing on the mobile device, where the particular software application is a native application that is configured to communicate with server system 130.

Physical Access Management System

Physical access management (PAM) system 150 manages, in conjunction with server system 130, physical access to one or more physical areas. PAM system 150 includes an entrance device 152 and a PAM server 154 to which entrance device 152 is communicatively coupled. Although only one entrance device is depicted, PAM system 150 may include multiple entrance devices.

Entrance device 152 is physically located near an entrance to a physical area to which a person may seek access. The entrance to the physical area may include a door, gate, or other object to prevent access to the physical area. The entrance may include a locking mechanism that locks the entrance (or otherwise prevents a person from entering the physical area). The locking mechanism unlocks the entrance based on data received from entrance device 152, as described in more detail below.

Entrance device 152 includes a code reader, such as a bar code reader or a QR code reader, that reads encoded data that is presented on a screen of client device 112. Additionally or alternatively, entrance device 152 includes a radio frequency (RF) receiver that receives an RF transmission from client device 112, which is configured to transmit the encoded data based on the encoded data that client device 112 received from server system 130. If a user is granted access, then a message is sent to the locking mechanism of the entrance to cause the entrance to be unlocked. This message may be sent by entrance device 152, PAM server 154, or server system 130.

In an embodiment, PAM system 150 is communicatively coupled to server system 130. For example, PAM server 154 is communicatively coupled to code generator 146 and/or data router 138. PAM server 154, upon receiving encoded data from entrance device 152, may communicate with data router 138 to verify that the encoded data is valid. Data router 138 (or another component of server system 130) decodes the encoded data and searches health-access database 144 based on the decoded data, searching for a matching data item. If a matching data item exists, then data router 138 informs PAM server 154.

In an alternative embodiment, instead of communicating with server system 130 to determine whether to grant access to the requesting user/client device, PAM server 154 receives a code from entrance device 152 and PAM server 154 makes a decision based on the code alone.

In an embodiment where the encoded data is an encrypted code data, PAM server 154 uses a public key to decrypt the encrypted code data to generate the original code data. PAM server 154 then makes a decision regarding whether to grant, to a user that presented the encoded data to entrance device 152, access to a physical area.

In the other non-encryption encoding techniques, PAM server 154 is able to decode the encoded data without a decryption key, such as using a bar code reader or a QR code reader to decode the encoded data.

In response to determining to grant access to a user that presents the encoded data to entrance device 152, PAM server 154 sends, to entrance device 152, a message indicating the grant. Entrance device 152, in turn, communicates with a locking mechanism of the entrance to cause the entrance to be unlocked. For example, the locking mechanism could be a bolt that extends from a door to a wall that is adjacent to the door. The locking mechanism causes the bolt to retreat inside the door, allowing a person to open the door without the bolt blocking the opening thereof.

Physical Access Grant Process Overview

Figure 3:
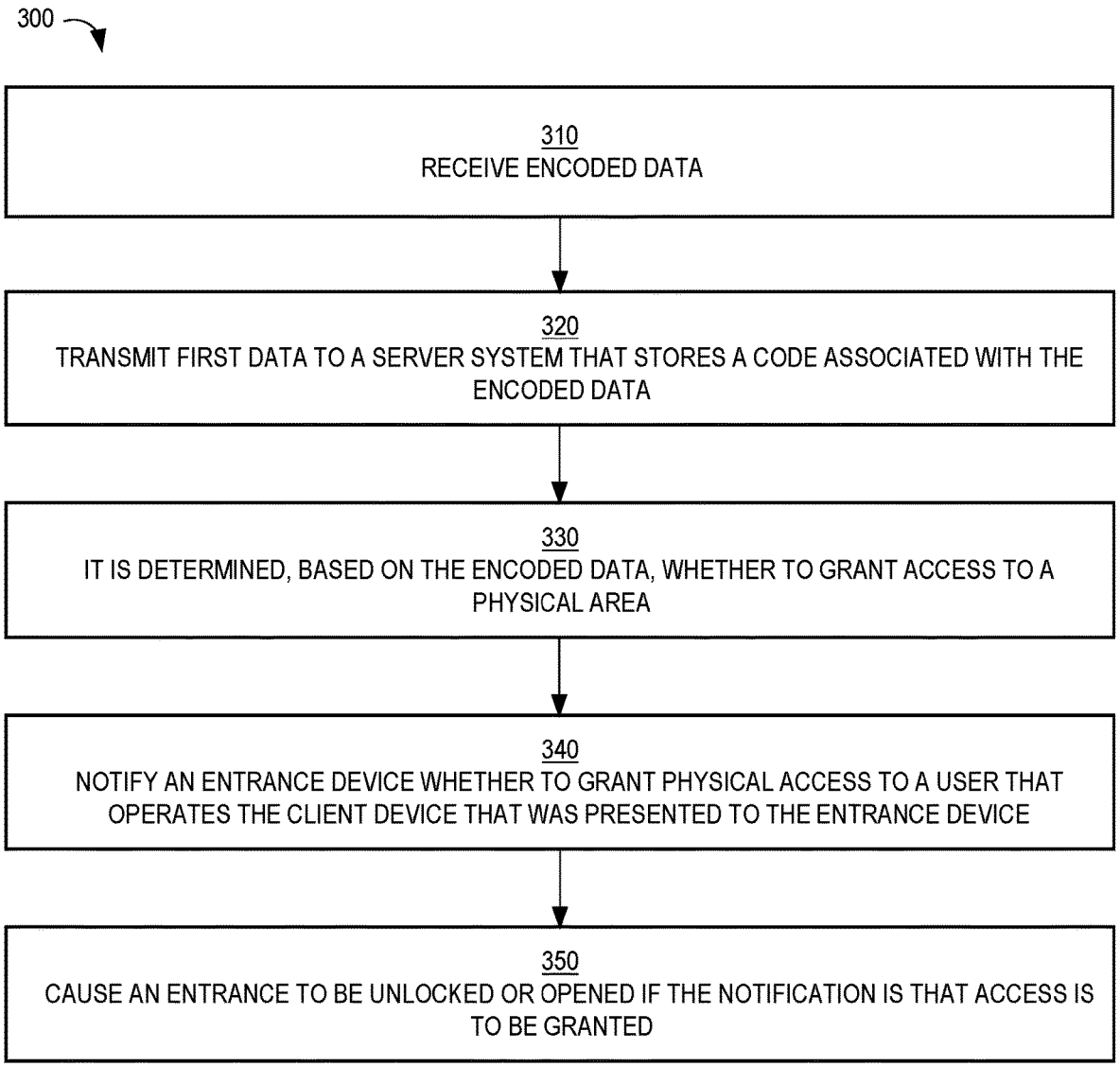
FIG. 3 is a flow diagram that depicts an example process for securely granting access to a physical area, in an embodiment.

FIG. 3 is a flow diagram that depicts an example process 300 for securely granting access to a physical area, in an embodiment. Process 300 may be performed by different elements of PAM system 150 and, optionally, of server system 130.

At block 310, encoded data is received. Block 310 may involve entrance device 152 reading encoded data that is presented on a screen of client device 112 or that is printed on a physical document. For example, a user provides, to client device 112, input (e.g., selection of one or more graphical buttons) that causes the encoded data to be presented on the screen. As another example, the user provides input that causes client device 112 to transmit a radio signal (that encodes the encoded data) that entrance device 152 is able to receive and process. As another example, a user presents a printed QR code (e.g., on paper) at an entrance device 152. Block 310 may also involve entrance device 152 sending the encoded data to PAM server 154.

At block 320, first data is transmitted to a server system (e.g., server system 130) that stores a code that is associated with the encoded data. The first data may be the encoded data or a decoded version of the encoded data. For example, in block 260, data router 138 encrypts the code that is generated with an encryption key. In this example, either PAM server 154 (a) decrypts the encrypted code and sends the decrypted code to server system 130 or (b) sends the encrypted code to server system 130. If the latter, then the encryption key may be a symmetric key, which server system 130 uses to decrypt the encrypted code; otherwise, the encryption key is a private key and PAM server 154 has a public key to decrypt the encrypted code. As another example, the encoded data is a QR code that entrance device 152 reads/decodes and sends to server system 130.

At block 330, it is determined whether to grant access to a physical area based on the encoded data. Block 330 may involve server system 130 first decoding the encoded data if PAM system 150 (e.g., entrance device 152) has not already done so. Block 330 may involve server system 130 looking up a corresponding record in health-access database 144 based on the decoded data.

At block 340, entrance device 152 is notified whether to grant access (to a physical area) to a user that operates the client device that was presented to entrance device 152. Block 340 may involve server system 130 transmitting grant data to PAM server 154, which determines a type of signal to transmit to entrance device 152 based on the content of the grant data.

At block 350, entrance device 152 causes an entrance to be unlocked or opened if the notification is that access is to be granted.

In process 300, server system 130 is involved. However, PAM system 150 may perform all the steps of receiving the encoded data, decoding the encoded data, and determining whether to grant physical access based on the decoded data. This is possible if server system 130 (e.g., data router 138) provides access data (e.g., a record from health-access database 144) to PAM system 150 upon generation of a code for a user and/or the user's computing device.

EXAMPLES

In the following examples, additional processes, systems, and methods are described in the context of a system for managing access to a physical area.

The following clauses and/or examples pertain to further embodiments or examples. Specifics in the examples may be used anywhere in one or more embodiments. The various features of the different embodiments or examples may be variously combined with some features included and others excluded to suit a variety of different applications. Examples may include subject matter such as a method, means for performing acts of the method, at least one machine-readable medium including instructions that, when performed by a machine cause the machine to perform acts of the method, or of an apparatus or system according to embodiments and examples described herein.

A first clause is a system for managing access to a physical area, the system includes one or more processor, one or more storage media storing instructions which, when executed by the one or more processors, cause, extracting first data from a digital file, based on identification data within the first data, searching a database and identifying, in the database, a data item that matches the identification data, associating the first data with the data item, after associating the first data with the data item, generating code data based on the association data, generating encoded data that encodes the code data, causing the encoded data to be sent, over a computer network, to a mobile device, or an account, of a user that is associated with the data item.

A further clause is the system of the first clause wherein the instructions, when executed by the one or more processors, further cause, receiving, by a device that is located near an entrance of a predetermined area, the encoded data from the mobile device, generating decoded data that is a decoded version of the encoded data, based on the decoded data, determining whether to allow the user to enter the predetermined area.

A further clause is the system of the clause above wherein the associating is performed by a first computer system that is remote from the device.

A further clause is the system of the clause above wherein the instructions, when executed by the one or more processors, further cause, based on receiving the encoded data, transmitting, by the device, to the first computer system, second data, after transmitting the second data to the first computer, receiving, by the device, from the first computer system, third data that indicates whether to allow the user to enter the predetermined area.

A further clause is the system of the clause above wherein: the second data is the encoded data; generating the decoded data is performed by the first computer system; and the instructions, when executed by the one or more processors, further cause identifying, by the first computer system, based on the decoded data, the first data.

A further clause is the system of the clause above wherein receiving the image data comprises receiving the image data from the mobile device that includes a digital camera that generated the image data.

A further clause is the system of the clause above wherein causing the encoded data to be sent comprises: transmitting a text message based on a phone number that is retrieved from the data item; transmitting an email message to an email address that is retrieved from the data item; or transmitting, based on an identifier for the mobile device, an application message to an application that is executing on the mobile device, wherein the identifier is retrieved from the data item.

A further clause is the system of the clause above wherein the physical document is a vaccine card.

A further clause is the system of the clause above wherein: the identification data comprises one or more names of the user; the first data comprises a dose date, a lot number, a vaccine type, or a clinic site.

A further clause is the system of the clause above wherein the encoded data is a bar code or a two-dimensional bar code.

A further clause is the system of the clause above wherein the database is an employee database that contains a plurality of data items, each data item corresponding to a different user of a plurality of users.

A second clause is a method for managing access to a physical area, the method includes: extracting first data from a digital file, based on identification data within the first data; searching a database and identifying, in the database, a data item that matches the identification data; associating the first data with the data item; after associating the first data with the data item, generating code data; generating encoded data that encodes the code data; and causing the encoded data to be sent, over a computer network, to a mobile device, or an account, of a user that is associated with the data item.

A further clause is the method of the second clause further comprising: receiving, by a device that is located near an entrance of a predetermined area, the encoded data from the mobile device; generating decoded data that is a decoded version of the encoded data, based on the decoded data; determining whether to allow the user to enter the predetermined area.

A further clause is the method of the clause above wherein the associating is performed by a first computer system that is remote from the device.

A further clause is the method of the clause above further comprising: based on receiving the encoded data, transmitting, by the device, to the first computer system, second data; after transmitting the second data to the first computer, receiving, by the device, from the first computer system, third data that indicates whether to allow the user to enter the predetermined area.

A further clause is the method of the clause above wherein: the second data is the encoded data; generating the decoded data is performed by the first computer system; and method further comprising identifying, by the first computer system, based on the decoded data, the first data.

A further clause is the method of the clause above wherein receiving the image data comprises receiving the image data from the mobile device that includes a digital camera that generated the image data.

A further clause is the method of the clause above wherein causing the encoded data to be sent comprises: transmitting a text message based on a phone number that is retrieved from the data item; transmitting an email message to an email address that is retrieved from the data item; or transmitting, based on an identifier for the mobile device, an application message to an application that is executing on the mobile device, wherein the identifier is retrieved from the data item.

A further clause is the method of the clause above wherein the physical document is a vaccine card.

A further clause is the method of the clause above wherein: the identification data comprises one or more names of the user; the first data comprises a dose date, a lot number, a vaccine type, or a clinic site.

A further clause is the method of the clause above wherein the encoded data is a bar code or a two-dimensional bar code.

A further clause is the method of the clause above wherein the database is an employee database that contains a plurality of data items, each data item corresponding to a different user of a plurality of users.

A third clause is one or more storage media storing instructions for managing access to a physical area, the one or more storage media storing instructions, when executed by one or more processors, causes: extracting first data from a digital file, based on identification data within the first data; searching a database and identifying, in the database, a data item that matches the identification data; associating the first data with the data item; after associating the first data with the data item, generating code data; generating encoded data that encodes the code data; and causing the encoded data to be sent, over a computer network, to a mobile device, or an account, of a user that is associated with the data item.

A further clause is the one or more storage media of the third clause further comprising: receiving, by a device that is located near an entrance of a predetermined area, the encoded data from the mobile device; generating decoded data that is a decoded version of the encoded data, based on the decoded data; determining whether to allow the user to enter the predetermined area.

A further clause is the one or more storage media of the clause above wherein the associating is performed by a first computer system that is remote from the device.

A further clause is the one or more storage media of the clause above further comprising: based on receiving the encoded data, transmitting, by the device, to the first computer system, second data; after transmitting the second data to the first computer, receiving, by the device, from the first computer system, third data that indicates whether to allow the user to enter the predetermined area.

A further clause is the one or more storage media of the clause above wherein: the second data is the encoded data; generating the decoded data is performed by the first computer system; and method further comprising identifying, by the first computer system, based on the decoded data, the first data.

A further clause is the one or more storage media of the clause above wherein receiving the image data comprises receiving the image data from the mobile device that includes a digital camera that generated the image data.

A further clause is the one or more storage media of the clause above wherein causing the encoded data to be sent comprises: transmitting a text message based on a phone number that is retrieved from the data item; transmitting an email message to an email address that is retrieved from the data item; or transmitting, based on an identifier for the mobile device, an application message to an application that is executing on the mobile device, wherein the identifier is retrieved from the data item.

A further clause is the one or more storage media of the clause above wherein the physical document is a vaccine card.

A further clause is the one or more storage media of the clause above wherein: the identification data comprises one or more names of the user; the first data comprises a dose date, a lot number, a vaccine type, or a clinic site.

A further clause is the one or more storage media of the clause above wherein the encoded data is a bar code or a two-dimensional bar code.

A further clause is the one or more storage media of the clause above wherein the database is an employee database that contains a plurality of data items, each data item corresponding to a different user of a plurality of users.

Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 4:
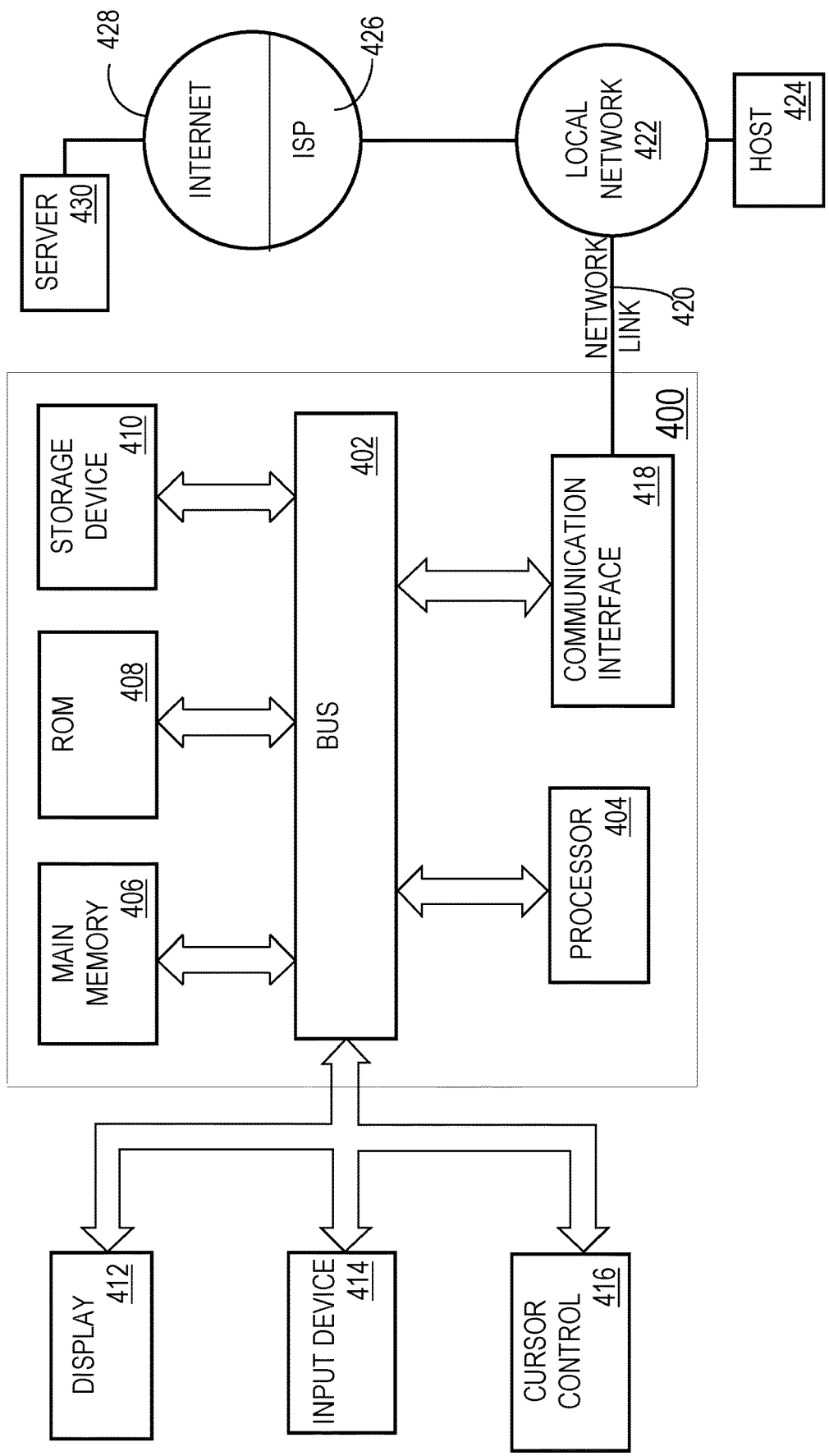
FIG. 4 is a block diagram that illustrates a computer system upon which an embodiment of the invention may be implemented.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A system for managing access to a physical area, the system comprising:
   one or more processors;
   one or more storage media storing instructions which, when executed by the one or more processors, cause:
   receiving a digital file from a mobile device that generated the digital file based on a physical document;
   extracting first data from the digital file;
   based on identification data within the first data, searching a database and identifying, in the database, a record associated with a user that matches the identification data;
   associating the first data with the record;
   after associating the first data with the record, generating code data comprising a unique identifier of a user that is associated with the record;
   generating encoded data that encodes the code data; and
   causing the encoded data to be sent, over a computer network, to a mobile device, or an account, of the user.

2. The system of claim 1, wherein the instructions, when executed by the one or more processors, further cause:
   receiving, by a device that is located near an entrance of a predetermined area, the encoded data from the mobile device;
   generating decoded data that is a decoded version of the encoded data;
   based on the decoded data, determining whether to allow the user to enter the predetermined area.

3. The system of claim 2, wherein associating the first data with the record is performed by a first computer system that is remote from the device.

4. The system of claim 3, wherein the instructions, when executed by the one or more processors, further cause:
   based on receiving the encoded data, transmitting, by the device, to the first computer system, second data;
   after transmitting the second data to the first computer system, receiving, by the device, from the first computer system, third data that indicates whether to allow the user to enter the predetermined area.

5. The system of claim 4, wherein:
   the second data is the encoded data;
   generating the decoded data is performed by the first computer system;
   the instructions, when executed by the one or more processors, further cause identifying, by the first computer system, based on the decoded data, the first data.

6. The system of claim 1, wherein:
   receiving the digital file comprises receiving image data from the mobile device that includes a digital camera that generated the image data.

7. The system of claim 1, wherein causing the encoded data to be sent comprises:
   transmitting a text message based on a phone number that is retrieved from the record;
   transmitting an email message to an email address that is retrieved from the record; or
   transmitting, based on an identifier for the mobile device, an application message to an application that is executing on the mobile device, wherein the identifier is retrieved from the record.

8. The system of claim 1, wherein the physical document is a vaccine card.

9. The system of claim 8, wherein:
   the identification data comprises one or more names of the user;
   the first data comprises a dose date, a lot number, a vaccine type, or a clinic site.

10. The system of claim 1, wherein the encoded data is a bar code or a two-dimensional bar code.

11. The system of claim 1, wherein the database is an employee database that contains a plurality of records, each record corresponding to a different user of a plurality of users.

12. A method for managing access to a physical area, the method comprising:
   receiving a digital file from a mobile device that generated the digital file based on a physical document;
   extracting first data from the digital file;
   based on identification data within the first data, searching a database and identifying, in the database, a record associated with a user that matches the identification data;
   associating the first data with the record;
   after associating the first data with the record, generating code data;
   generating encoded data that encodes the code data;

causing the encoded data to be sent, over a computer network, to a mobile device, or an account, of a user that is associated with the record;

wherein the method is performed by one or more computing devices.

13. The method of claim 12, further comprising:

receiving, by a device that is located near an entrance of a predetermined area, the encoded data from the mobile device;

generating decoded data that is a decoded version of the encoded data;

based on the decoded data, determining whether to allow the user to enter the predetermined area.

14. The method of claim 13, wherein associating the first data with the record is performed by a first computer system that is remote from the device.

15. The method of claim 14, further comprising:

based on receiving the encoded data, transmitting, by the device, to the first computer system, second data;

after transmitting the second data to the first computer system, receiving, by the device, from the first computer system, third data that indicates whether to allow the user to enter the predetermined area.

16. The method of claim 15, wherein:

the second data is the encoded data;

generating the decoded data is performed by the first computer system;

the method further comprising identifying, by the first computer system, based on the decoded data, the first data.

17. The method of claim 12, wherein receiving the digital file comprises receiving image data from the mobile device that includes a digital camera that generated the image data.

18. The method of claim 12, wherein causing the encoded data to be sent comprises:

transmitting a text message based on a phone number that is retrieved from the record;

transmitting an email message to an email address that is retrieved from the record; or transmitting, based on an identifier for the mobile device, an application message to an application that is executing on the mobile device, wherein the identifier is retrieved from the record.

19. The method of claim 18, wherein:

the physical document is a vaccine card;

the identification data comprises one or more names of the user indicated on the vaccine card;

the first data comprises a dose date, a lot number, a vaccine type, or a clinic site indicated on the vaccine card.

20. One or more storage media storing instructions for managing access to a physical area, the instructions, when processed by one or more processors, cause:

extracting first data from a digital file;

based on identification data within the first data, searching a database and identifying, in the database, a record that matches the identification data;

associating the first data with the record;

after associating the first data with the record, generating code data comprising a unique identifier of a user that is associated with the record;

generating encoded data that encodes the code data;

causing the encoded data to be sent, over a computer network, to a mobile device, or an account, of a user that is associated with the record.

* * * * *